US012575730B2

(12) United States Patent
Laforest et al.

(10) Patent No.: US 12,575,730 B2
(45) Date of Patent: Mar. 17, 2026

(54) OPHTHALMIC SYSTEM AND METHOD FOR CLINICAL DEVICE USING TRANSCLERAL ILLUMINATION WITH MULTIPLE POINTS SOURCE

(71) Applicant: ECOLE POLYTECHNIQUE FEDERALE DE LAUSANNE (EPFL), Lausanne (CH)

(72) Inventors: Timothé Laforest, Crozet (FR); Christophe Moser, Lausanne (CH); Mathieu Kunzi, Geneva (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 1190 days.

(21) Appl. No.: 17/312,819

(22) PCT Filed: Dec. 12, 2019

(86) PCT No.: PCT/IB2019/060707
§ 371 (c)(1),
(2) Date: Mar. 21, 2022

(87) PCT Pub. No.: WO2020/121243
PCT Pub. Date: Jun. 18, 2020

(65) Prior Publication Data
US 2022/0248952 A1     Aug. 11, 2022

(30) Foreign Application Priority Data
Dec. 12, 2018     (WO) .................. PCT/IB2018/059951

(51) Int. Cl.
*A61B 3/12* (2006.01)
*A61B 3/14* (2006.01)

(52) U.S. Cl.
CPC ............ *A61B 3/1225* (2013.01); *A61B 3/145* (2013.01)

(58) Field of Classification Search
CPC ......... A61B 3/113; A61B 3/12; A61B 3/1225; A61B 3/0008; A61B 3/102; A61B 3/0025;
(Continued)

(56) References Cited

U.S. PATENT DOCUMENTS 6,726,325 B2     4/2004  Xie et al.
6,736,508 B2     5/2004  Xie et al.
(Continued)

FOREIGN PATENT DOCUMENTS

CN     101799874     * 3/2010 ............... G06K 9/62
JP     2006-522653 A     10/2006
(Continued)

OTHER PUBLICATIONS

Advances in Imaging and Electron Physics, vol. 146, "Spiral Phase Microscopy", Edited by Peter W. Hawkes, Academic Press, 2007.
(Continued)

*Primary Examiner* — Brandi N Thomas
(74) *Attorney, Agent, or Firm* — Nixon & Vanderhye PC

(57)     ABSTRACT
An ophthalmic illumination and imaging system with transscleral/transpalpebral illumination of the eye fundus comprises a light-delivering device with a plurality of emitting areas; each of the emitting areas being configured to be independently controllable and directed towards the sclera of the intended eye to measure, providing transscleral oblique illumination of the eye fundus; an active eye aberration correcting system; and an imaging system configured to create multiple images of the eye fundus on multiple imaging sensors.

20 Claims, 6 Drawing Sheets

(58) Field of Classification Search

CPC ..... A61B 3/1015; A61B 3/145; A61B 3/1025; A61B 3/152; A61B 2090/365; A61B 2562/0204; A61B 2562/0219; A61B 2562/0247; A61B 3/005; A61B 3/022; A61B 3/024; A61B 3/028; A61B 3/0285; A61B 3/032; A61B 3/036; A61B 3/063; A61B 3/066; A61B 3/08; A61B 3/085; A61B 3/10; A61B 3/1005; A61B 3/101; A61B 3/103; A61B 3/1035; A61B 3/1216; A61B 3/1241; A61B 3/13; A61B 3/14; A61B 3/165; A61B 5/0059; A61B 5/0066; A61B 5/0077; A61B 5/01; A61B 5/12; A61B 5/14532; A61B 5/1455; A61B 5/14555; A61B 5/361; A61B 5/369; A61B 5/398; A61B 5/6803; A61B 8/10; A61B 8/46; A61B 8/461; G02B 2027/0138; G02B 2027/014; G02B 2027/0185; G02B 2027/0187; G02B 21/0032; G02B 27/0093; G02B 27/017; G02B 27/0172; G02B 27/0179; A61F 2007/0004; A61F 2007/004; A61F 2009/00863; A61F 9/0026

See application file for complete search history.

(56) References Cited

U.S. PATENT DOCUMENTS

| | | | |
|---|---|---|---|
| 7,387,385 B2 | 6/2008 | Sander | |
| 7,758,189 B2 | 7/2010 | Hammer et al. | |
| 8,696,122 B2 | 4/2014 | Hammer et al. | |
| 8,857,988 B2 | 10/2014 | Sharma et al. | |
| 9,033,510 B2 | 5/2015 | Narasimha-Lyer et al. | |
| 2002/0097377 A1 | 7/2002 | Kudryashov et al. | |
| 2004/0196399 A1 | 10/2004 | Stavely | |
| 2007/0030448 A1 | 2/2007 | Biernat et al. | |
| 2007/0159600 A1 | 7/2007 | Gil et al. | |
| 2014/0334707 A1 | 11/2014 | Teiwes et al. | |
| 2015/0055094 A1 | 2/2015 | Boate et al. | |
| 2017/0265742 A1 | 9/2017 | Nozato et al. | |

FOREIGN PATENT DOCUMENTS

| | | | | | |
|---|---|---|---|---|---|
| JP | 2012161382 | * | 2/2011 | ............. | A61B 3/102 |
| WO | 2017/151921 A1 | | 9/2017 | | |
| WO | 2017/195163 A1 | | 11/2017 | | |
| WO | WO 2017195163 | * | 11/2017 | ........... | A61B 3/0008 |
| WO | 2018/022521 | | 2/2018 | | |
| WO | 2018/197288 A1 | | 11/2018 | | |

OTHER PUBLICATIONS

Caetano Dos Santos, Florentino Luciano, et al., "Fully automated detection, segmentation, and analysis of in vivo RPE single cells", Eye, vol. 35, 2021, pp. 1473-1481.

Chui, Toco Y. P., et al., "The use of forward scatter to improve retinal vascular imaging with an adaptive optics scanning laser ophthalmoscope", Biomedical Optics Express, vol. 3, No. 10, Oct. 1, 2012, pp. 2537-2549.

Chui, Toco Y. P., et al., "Imaging of Vascular Wall Fine Structure in the Human Retina Using Adaptive Optics Scanning Laser Ophthalmoscopy", IOVS, vol. 54, No. 10, Oct. 2013, pp. 7115-7124.

Ferguson, R. Daniel, et al., "Adaptive optics scanning laser ophthalmoscope with integrated wide-field retinal Imaging and tracking", J. Opt. Soc. Am. A: Opt. Image Sci. Vis., vol. 27, No. 11, Nov. 1, 2010, pp. A265-A277.

Kocaoglu, Omer P., et al., "Adaptive optics optical coherence tomography with dynamic retinal tracking", Biomedical Optics Express, vol. 5, No. 7, Jul. 1, 2014, pp. 2262-2284.

Laforest, Timothé, et al., "Transscleral optical phase imaging of the human retina", Nature Photonics, vol. 14, 2020, pp. 439-445.

Lingenfelder, Christian, et al., "Transscleral LED illumination pen", Biomedical Engineering Letters, vol. 7, 2017, pp. 311-315.

Maurer, Christian, et al., "What spatial light modulators can do for optical microscopy", Laser & Photonics Reviews, vol. 5, No. 1, 2011, pp. 81-101.

Sahin, Betul, et al., "Adaptive optics with pupil tracking for high resolution retinal imaging", Biomedical Optics Express, vol. 3, No. 2, Feb. 1, 2012, pp. 225-239.

Schalenbourg, A., et al., "Pitfalls in colour photography of choroidal tumours", Eye, vol. 27, No. 2, 2013, pp. 224-229.

Scoles, Drew, et al., "In vivo dark-field imaging of the retinal pigment epithelium cell mosaic", Biomedical Optics Express, vol. 4, No. 9, Sep. 1, 2013, pp. 1710-1723.

Sheehy, Christy K., et al., "Active eye-tracking for an adaptive optics scanning laser ophthalmoscope", Biomedical Optics Express, vol. 6, No. 7, Jul. 1, 2015, pp. 2412-2423.

Steiger, Ruth, et al., "SLM-based off-axis Fourier filtering in microscopy with white light illumination", Optics Express, vol. 20, No. 14, Jul. 2, 2012, pp. 15377-15384.

Toslak, Devrim, et al., "Trans-palpebral illumination: an approach for wide-angle fundus photography without the need for pupil dilation", Optics Letters, vol. 41, No. 12, Jun. 15, 2016, pp. 2688-2691.

International Search Report and Written Opinion of the ISA for PCT/IB2019/060707 dated Apr. 17, 2020, 8 pages.

Written Opinion of the IPEA PCT/IB2019/060707 dated Nov. 16, 2020, 5 pages.

* cited by examiner

OPHTHALMIC SYSTEM AND METHOD FOR CLINICAL DEVICE USING TRANSSCLERAL ILLUMINATION WITH MULTIPLE POINTS SOURCE

This application is the U.S. national phase of International Application No. PCT/IB2019/060707 filed Dec. 12, 2019 which designated the U.S. and claims priority to IB Patent Application No. PCT/IB2018/059951 filed Dec. 12, 2018, the entire contents of each of which are hereby incorporated by reference.

FIELD OF THE INVENTION

The present invention relates to oblique transscleral illumination of the retina with several (physical point) light sources around the eye allowing for dark field imaging, high resolution imaging, large field of view imaging and retinal tracking.

BACKGROUND

We described in PCT/IB2017/052803, System, method and apparatus for retinal absorption phase and dark field imaging with oblique illumination, the methods for transscleral illumination, allowing for dark field and phase gradient techniques by using the scattering properties of the fundus.

Current ophthalmic devices based on OCT, OCT Angiography and SLO have tracking system implemented thanks to a scanning beam which is adjusted. The retinal tracking systems described in the context of ophthalmic instruments consist of a way to monitor the retina and measure its displacement, coupled to a way to actively keep the retina imaging zone still, even when the eye is moving. These systems are usually also able to actively direct the imaging zone wherever the operator chose to image (within given limits) even when the patient cannot fixate a target.

SLO system coupled with a tracking system and adaptive optics are described in U.S. Pat. No. 7,758,189 B2, STABILIZED RETINAL IMAGING WITH ADAPTIVE OPTICS, where a first module tracks a reference feature in the eye, and a second module control the light beam in order to move the imaging beam to the reference feature. Relevant publication about the same system 'Adaptive optics scanning laser ophthalmoscope with integrated wide-field retinal imaging and tracking', *J. Opt. Soc. Am. A,* 27(11), 2010. It includes a large field of view imaging feature (>25° at the retina). A competitive method for retinal tracking at 960 Hz is also presented in 'Active eye-tracking for an adaptive optics scanning laser ophthalmoscope', *Biomed. Opt. Exp.,* 6(7), 2015.

Retinal tracking has also been implemented in OCT and OCT Angiography systems, such as described in U.S. Pat. No. 6,726,325 B2, TRACKING ASSISTED OPTICAL COHERENCE TOMOGRAPHY, U.S. Pat. No. 6,736,508 B2, TRACKING ASSISTED OPTICAL PROCEDURE, U.S. Pat. No. 8,857,988 B2 DATA ACQUISITION METHODS FOR REDUCED MOTION ARTIFACTS AND APPLICATIONS IN OCT ANGOGRAPHY. An OCT device coupled to eye tracking is detailed in US 2014/0334707 A1, METHOD AND APPARATUS FOR IMAGE-BASED EYE TRACKING FOR RETNAL DIAGNOSTIC OR SURGERY DEVICE or U.S. Pat. No. 9,033,510 B2, SYSTEMIS AND METHODS FOR EFFICIENTLY OBTAINING MEASUREMENTS OF THE HUMAN EYE USING TRACKING.

More recently, OCT modality has been coupled to both SLO system to have a large field of view, and to adaptive optics. An AO-OCT system integrating retinal tracking is for instance presented in 'Adaptive optics optical coherence tomography with dynamic retinal tracking', *Biomed. Opt. Exp.,* 5(7), 2014. A system including OCT, SLO and retinal tracking is detailed in U.S. Pat. No. 8,696,122 B2 MULTIFUNCTIONAL ADAPTIVE OPTICS RETNAL IMAGING.

The method presented in PCT WO2018197288A1 Systeme et méthode d'imagerie rétinienne multi-echelle, is a multi-scale device, with several illumination modules coupled with a scanning system. In this invention, the scanning system is made by either a SLO or OCT methods with adaptive optics.

The principle described in 'Adaptive optics with pupil tracking for high resolution retinal imaging' *Biomed. Opt. Exp.* 2(3), 2012 uses the information from the pupil displacement to correct the eye aberrations with adaptive optics. It includes a camera-based system to track the pupil position.

Fundus camera systems have been developed using transscleral illumination or transpalpebral illumination. The PCT WO 2017/151921A1 METHODS AND DEVICES FOR FUNDUS PHOTOGRAPHY EMPLOYING TRANSPALPEBRAL AND TRANS-SCLERAL ILLUMINATION describes a wide field transscleral or transpalpebral system using different apparatus for the light projection system and shapes and the sclera/skin tissues. The PCT JP2006522653A Illumination method and system of the eye via a scleral also presents a fundus imaging system by projection a beam on the sclera. The company Annidis has also a commercial device using transscleral illumination for imaging the choroid US2015/0055094A, METHOD AND APPARATUS FOR IMAGING THE CHOROID. In 2017, Lingenfelder et al. presented a transscleral illumination system using LEDs 'Transscleral LED illumination pen', *Biomed. Eng. Lett.* 7, 2017.

Finally, the patent US 2004/0196399 A1, DEVICE INCORPORATING RETINA TRACKING, describes a device integrating a retina tracking system which is used to determine the direction of a user's gaze upon the microdisplay.

The contrast of a phase object can be increased by performing a filtering a the Fourier plane (or pupil plane). The principle has been demonstrated for microscopy in the following publications: What spatial light modulators can do for microscopy, Lasers and Photonics Reviews 5, 81-101 (2011), Spiral phase microscopy, Advances in Imaging and Electron Physics 146, 1-20 (2007); Ed. P. Hawkes, Academic Press (ISBN-13: 978-0-12-373908-7), and SLM-based off-axis Fourier filtering in microscopy with white light illumination, Opt. Exp., 20(14), 2012.

The said transscleral methods above are described using one illumination point or sometimes with two illumination points where the two point-sources provide illumination simultaneously or not. Here, by point, we mean "point-source like" such as a small area. We mean any propagating light beam illuminating a specific part of the eye/eyelid(s) or even the entire eye/eyelid(s).

None of the systems above provides a system using a transscleral illumination to provide simultaneously a high resolution—adaptive optics corrected—image and a large field of view to perform retinal tracking.

None of the inventions above use a tracking system implemented in a multipixel sensor camera-based retinal imaging system (full-field) coupled to adaptive optics.

SUMMARY OF THE INVENTION

The invention provides an ophthalmic illumination and imaging system with transscleral/transpalpebral illumination of the eye fundus. The system comprises a light-delivering device with a plurality of emitting areas; each of the emitting areas being configured to be independently controllable and directed towards the sclera of the intended eye to measure, providing transscleral oblique illumination of the eye fundus; an active eye aberration correcting system; and an imaging system configured to create multiple images of the eye fundus on multiple imaging sensors.

In a preferred embodiment, the system further comprises an active tracking system configured to track a movement of the eye fundus and configured to stabilize spatially at least one of the multiple images of the eye fundus.

In a further preferred embodiment, the tracking system comprises a tracking sensor measuring the movement of the eye fundus and a tracking corrector configured to correct the at least one of the multiple images spatially stabilized for the movement.

In a further preferred embodiment, the system further comprises a sequential switch configured to sequentially turn on one of the plurality of emitter areas at a time and enable a corresponding sequence in time of the eye fundus images created by the imaging system.

In a further preferred embodiment, the active the eye aberrations correcting system comprises a wavefront sensor and a wavefront corrector.

In a further preferred embodiment, the multiple images are produced with the light-delivering device.

In a further preferred embodiment, a measure of the movement of the eye is made using at least one of the multiple eye fundus images.

In a further preferred embodiment, a correction of the movement of the eye is made by tilting a mirror located at an optically conjugated eye pupil plane.

In a further preferred embodiment, the correction of the eye movement is made using the tilting ability of the wavefront corrector used for the active correction of the eye aberrations.

In a further preferred embodiment, the correction of the eye movement is made using a 2-axis tilting the full wavefront corrector with an external rotation stage.

In a preferred embodiment, the correction of the eye movement is made using a 2-axis tilting of a mirror which is not the wavefront corrector.

In a further preferred embodiment, multiple imaging paths making the multiple eye fundus images are separated thanks to a beam splitter or a dichroic mirror.

in a further preferred embodiment, the light-delivering device contains a light diffuser.

In a further preferred embodiment, the diffuser integrated in the light-delivering device is used to obtain a few millimeters wide spot on the sclera or skin surface.

In a further preferred embodiment, the diffuser is moving to produce temporal averaging of the speckle noise.

In a further preferred embodiment, a wavelength of the light delivering device is chosen in the transmission range of the sclera-choroid-skin approximately from 400 nm to 1200 nm.

In a further preferred embodiment, the light delivering device comprises a plurality of elementary components such as light emitting diode, superluminescent diode, organic light emitting diode, optical fibers.

In a further preferred embodiment, individual emitting areas have a different temporal spectrum of emission from one to another.

In a further preferred embodiment, individual emitting areas have a different angular spectrum of emission from one to another.

In a further preferred embodiment, the system further comprises a camera configured to record interference from one or several exit beams from the pupil and an additional reference beam extracted from the light-delivering device before entering the eye.

In a further preferred embodiment, a non-uniform phase or absorption object is placed in a conjugated pupil plane to increase the phase contrast.

BRIEF DESCRIPTION OF THE DRAWINGS

The invention will be better understood through the detailed description hereunder and in reference to the appended drawings. The content of the drawings is briefly explained hereunder.

DETAILED DESCRIPTION

Overview

Figure 1:
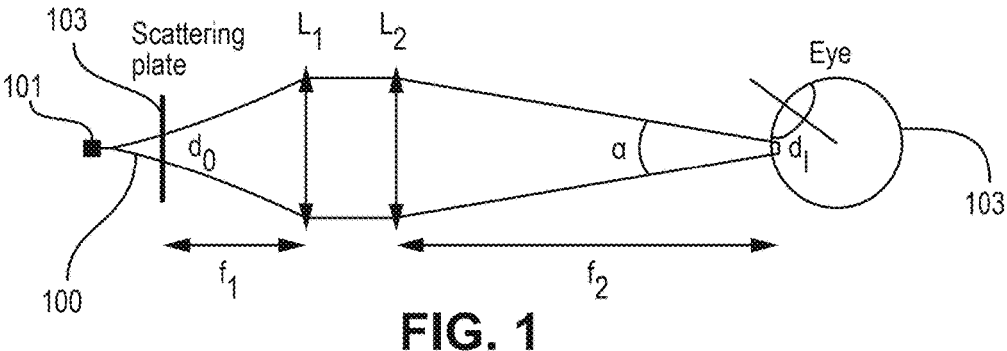
FIG. 1 shows an optical system including a diffuser according to an example embodiment of the invention.

This present invention relates to an ophthalmic system and method based on transscleral illumination coupled to adaptive optics and a retinal tracking feature. The system may comprise a retinal camera imaging the retina with high resolution, with a digital sampling smaller than 2 μm/pixel and a retinal camera imaging the retina over a larger field of view (typically more than 30°), with a digital sampling of 20 μm/pixel. In addition, the imaging system includes an adaptive optics loop in order to correct the aberration of the eye. The adaptive optics loop is implemented with, but not limited to, a Shack-Hartmann wavefront sensor and a deformable mirror. The wavefront sensor senses in real time the aberrations and send the control feedback to the deformable mirror. The tracking system is implemented thanks to 2 axis tilting mirror (or tip/tilt platform) in a relayed pupil plane of the imaging system with the large field of view image as feedback to compute the tilts.

Instead of using the eye lens as part of the illumination path, different layers of the eye (the retina, the choroid, the sclera and the skin) are used as transmissive scattering layers for the illumination. The following scheme is presented as embodiments:

The light is passing through the skin layer near the eye, sclera, the choroid and the retina. The transmitted scattered light illuminates the fundus. No light is entering the pupil-lens. The light delivering device is contactless.

The optical device delivering the propagating light beam (hereafter referred as "beam") on the sclera or on the skin is designed to make a focal spot or any delimited light surface shape (hereafter referred as "spot") on the said sclera or skin, the spot diameter being a few millimeters.

The optical device delivering the beam on the sclera or on the skin is designed with a diffusing element to reduce the spatial coherence of the source and the diffuser is moving in order to average the speckle patterns over time on the sensor.

The retinal tracking system works as a closed loop with the large field of view (hereafter referred as "FOV") image serves as feedback. The large FOV camera is the tracking sensor.

The retinal tracking system is implemented thanks to a two axis tilting actuator on which a light reflective surface (hereafter referred as "mirror") is mounted, and placed at an optically conjugated pupil plane. The mirror placed on the tilting actuators is the tracking corrector.

The conjugated pupil plane used to perform the retinal tracking is the correction plane of the adaptive optics loop.

The adaptive optics and retinal tracking loops are connected.

The large FOV image is obtained with the same transscleral illumination as the high-resolution image, simultaneously.

The imaging optical path is split with most of the power going to the high-resolution path in order to keep a good SNR on the high-resolution image, while having a good contrast on the large FOV image.

The ratio of power between the large FOV beam and the high-resolution beam is, but not limited to, 4% for large FOV, 96% for high resolution.

The phase contrast image of the transparent layers of the retina is enhanced by a phase or absorption pattern inserted in the pupil plane.

The detection is made by making an interference on a sensor, between one or several transscleral illumination sources and a reference beam.

The optical sectioning at the photoreceptors/RPE layers is provided by the combination of through pupil/transscleral illumination.

The transscleral beam is shaped in order to maximize the optical transmission through the eye tissues.

Illumination is provided thanks to a single or a combination of light sources in the range, but not limited to, 400 to 1200 nm. Such sources are, but not limited to: light emitting diode, organic light emitting diode, super luminescent emitting diode, quantum dot source, a lamp, a black body radiation source, a side emitting fiber, a forward emitting fiber with an element directing the light to the skin. Different sources in the same delivering device can provide the same or different spectrum of illumination.

Illumination Methods and Apparatus

Configuration 1

Referring to FIG. 1, an illumination beam 100 is provided thanks to a laser diode coupled to a multimode fiber 101. The output of the multimode fiber 101 illuminates a light diffuser 102 (scattering plate) in order to cover a disc of diameter d0 on the light diffuser 102. The extended source generated by the d0 diameter disc emits a beam which is collimated thanks to a first lens L1, a second lens L2 forms an image on the sclera 103 or skin of the d0 diameter disc, with a corresponding diameter dl.

Figure 2:
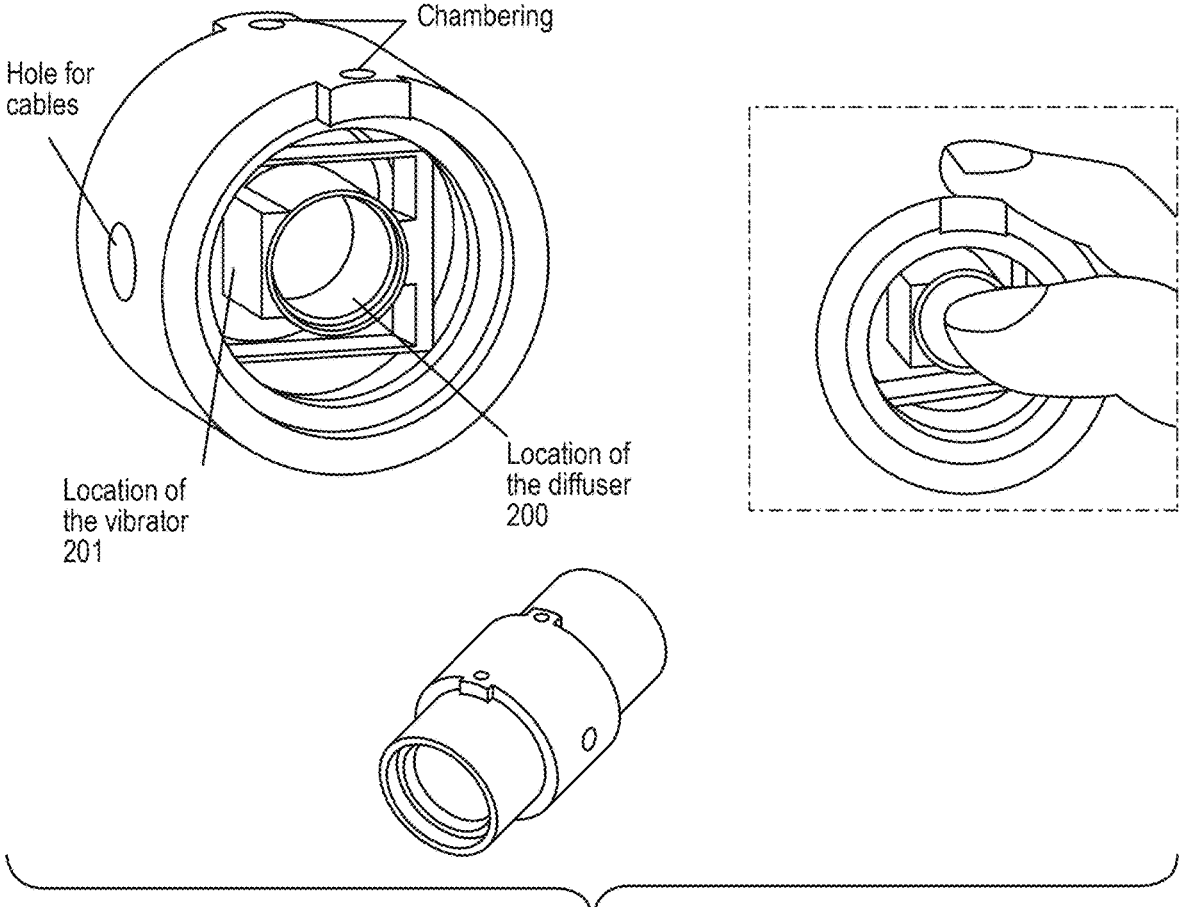
FIG. 2 shows a photograph and design of a designed prototype with 2 lenses and a diffuser, wherein the light is provided by a multimode fiber connected to the optical system.

Referring to FIG. 2, to average speckle grains produced by the spatially coherent light of the laser diode, the diffuser may be mounted on a moving plate 200, actuated by a vibrator 201. The vibrator 201 makes the speckle pattern moving faster than the integration time of the imaging camera (not represented in FIG. 2). The figure shows an example of design to be integrated with 1-inch lenses.

Configuration 2

Figure 3:
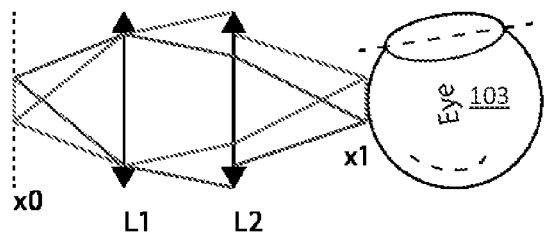
FIG. 3 illustrates a system projecting the light on the sclera, wherein the light provides from a light emitting diode (LED).

Referring to FIG. 3, the system projecting the light on the sclera 103 is a light emitting diode (LED) (LED not illustrated in the Figure). The LED device produces a squared extended source of side x0, collimated by a first lens L1, and imaged on the sclera 103 or skin by a lens L2. The image of the LED is a square of side x1.

Imaging Apparatus

Configuration 1

Figure 4:
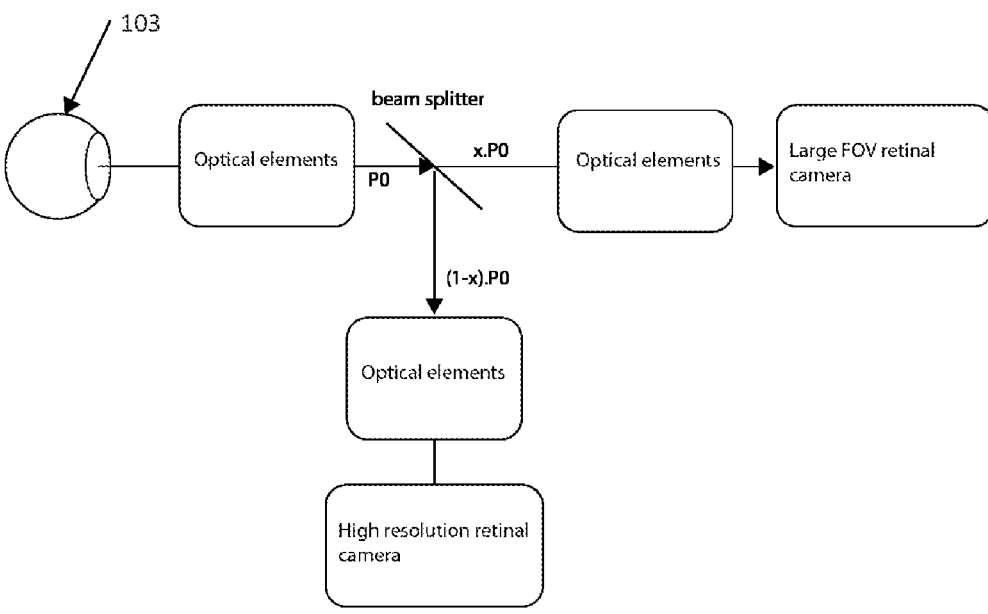
FIG. 4 schematically illustrates a setup for generating a large field of view (FOV) and a small field of view images simultaneously from 2 separated imaging paths, according to the invention.

Referring to FIG. 4, the large field of view (FOV) and small field of view images are generated simultaneously by 2 separated imaging paths. The separation is performed by placing a slipping optical element which uses a small portion x0 of the total light flux to obtain the large field of view image.

Configuration 2

Figure 5:
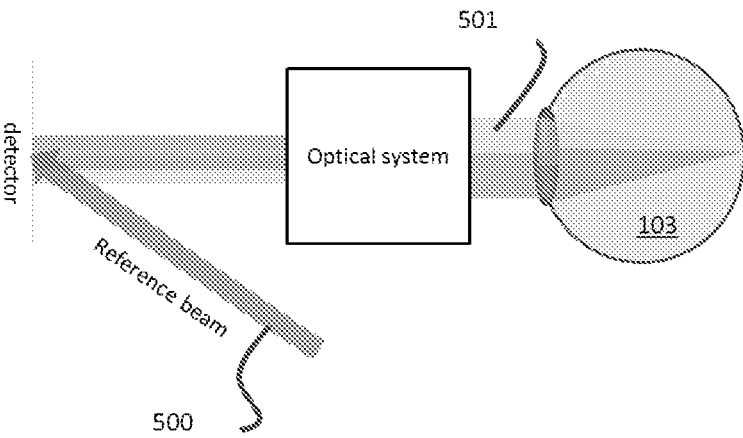
FIG. 5 shows a scheme for measuring an interference.

Referring to FIG. 5, the image after transscleral illumination is obtained by superimposing a reference beam 500 to the beam 501 coming out from the eye/retina 103. The final image is extracted from the interference.

Configuration 3

Figure 6:
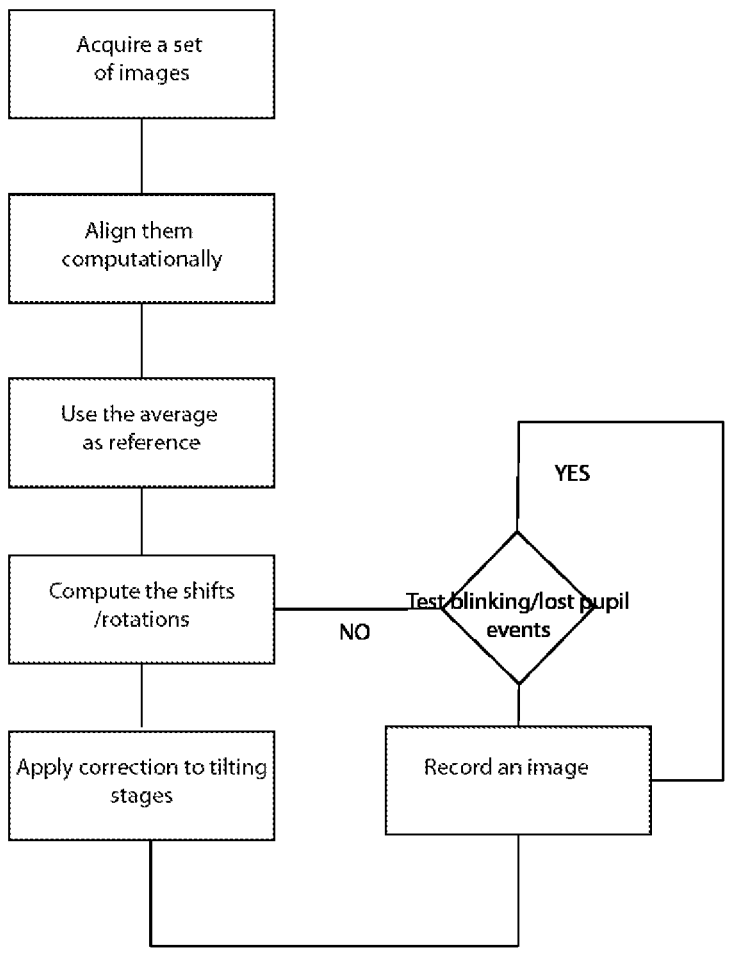
FIG. 6 contains an example of flow chart of a retinal tracking process.
Figure 7:
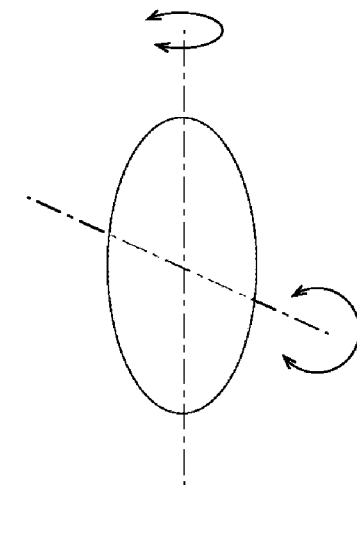
FIG. 7 contains an illustration of tilting plane of the conjugated pupil plane.

Referring to FIG. 6, this serves to illustrate that a tracking system is implemented following the presented flow chart. A set of images is acquired, and subsequently the images are aligned. An average computed from the set is used as a reference from now on. In a following step shifts and rotation are computed. Correction is then applied to tiling images and an image recorded. The large field of view imaging system provides the feedback to the tracking corrector/actuator. If events such as blinking or pupil lost occur, the tracking loop is held on. Referring to FIG. 7, this contains a schematic illustration of the tracking actuator or corrector. The actuator is configured to be placed at a conjugated pupil plane and generate tilts along two orthogonal directions.

Configuration 4

Figure 8:
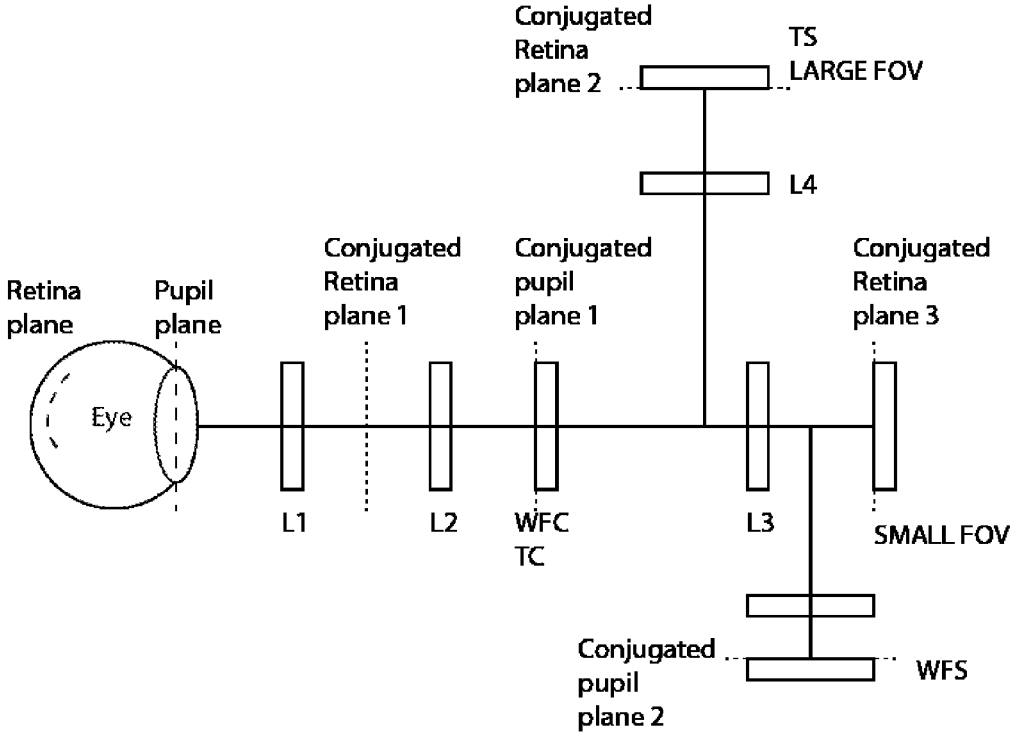
FIG. 8 shows an optical arrangement for large FOV and small FOV imaging path coming from transscleral illumination.

Referring to FIG. 8, this shows an optical arrangement combining wavefront correction and retinal tracking. The wavefront correction closed loop is composed of a wavefront sensor (WFS) and a wavefront corrector (WFC). The retinal tracking is composed of the large field of view acquisition device, used as the tracking sensor (TS) and a tracking corrector (TC). In the example, the tracking corrector and the wavefront corrector are combined in a single device, which can be a deformable mirror, a spatial light modulator.

Alternatively, the WFS sensor and may also directly measure the tilts to perform the retinal tracking.

Figure 9:
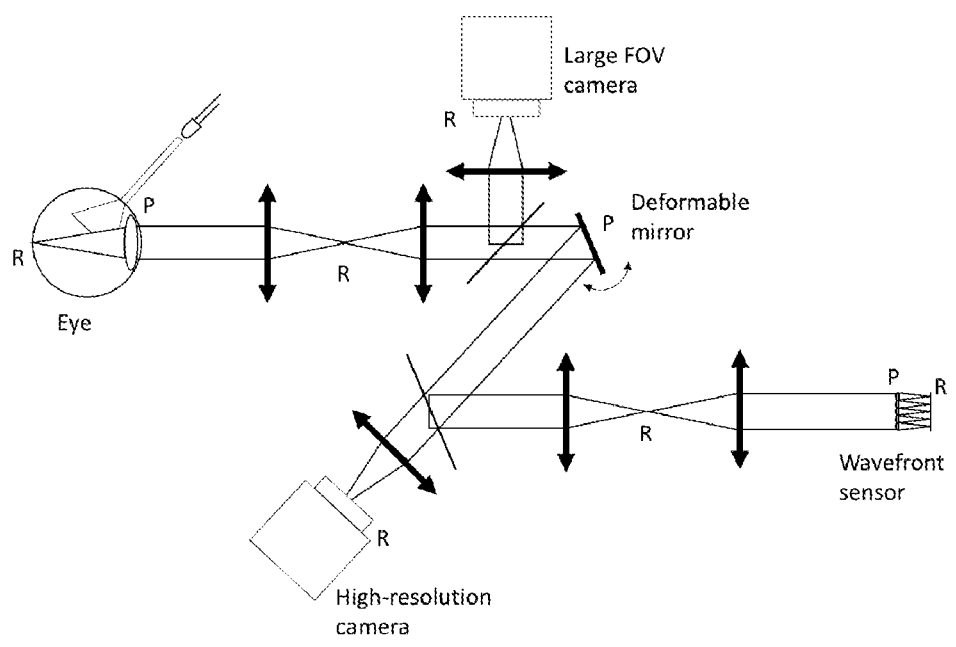
FIG. 9 shows a layout example according to the invention, using wavefront corrector plane as the tracking corrector plane.

Referring to FIG. 9, this shows a layout example according to the invention. After being lit by the transscleral illumination, the retina R is imaged through the eye pupil P. The system is composed of two different scales imaging paths ending with a large FOV camera and a high-resolution camera. The wavefront aberration correction system is composed of a Shack-Hartmann wavefront sensor and a deformable mirror wavefront corrector. The retina tracking system is composed of the large FOV camera that serves as the tracking sensor and of the deformable mirror serving as the tracking corrector. The deformable mirror produces the tilts used for tracking correction either using the deformation of its reflective membrane and/or by being located on top of a two-axis rotation stage.

Figure 10:
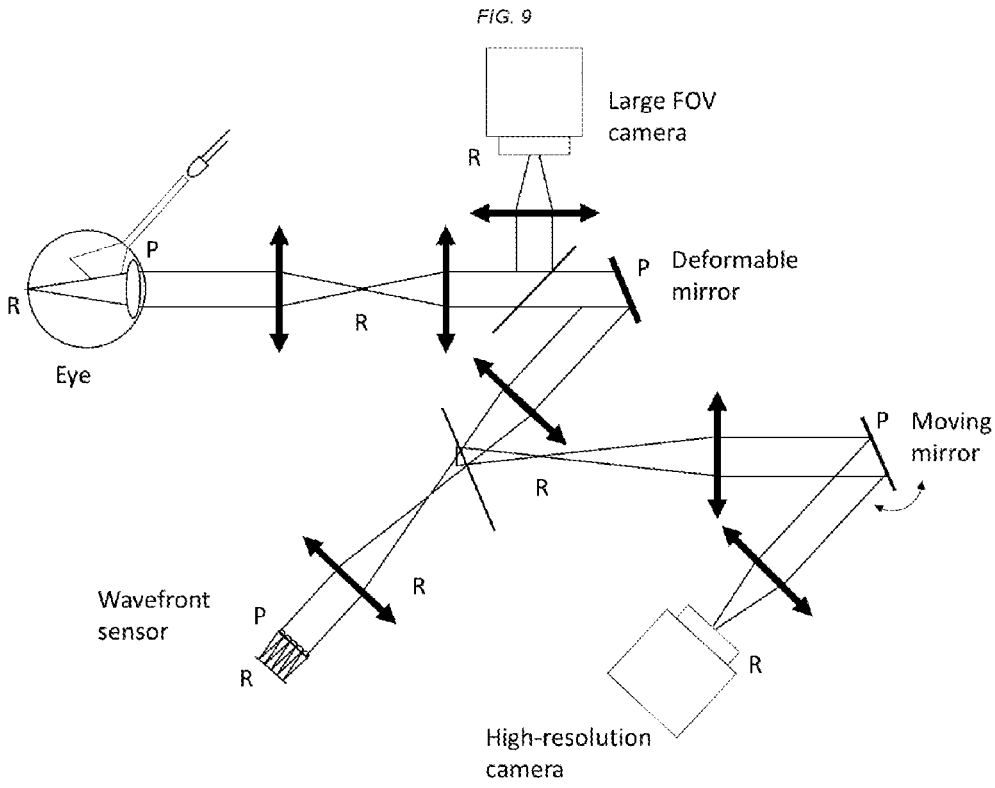
FIG. 10 shows a layout example of the presented invention using a tracking corrector in a different pupil plane.

Referring to FIG. 10, another layout example according to the invention is shown. The description is the same as with FIG. 9 except for the retina tracking corrector. In this example, a moving mirror serves as tracking corrector, but this mirror is not the wavefront corrector used in the wavefront aberration correction system. The moving mirror is located at a pupil conjugated plane and is composed of a regular planar mirror placed on a two-axis rotation stage.

Configuration 5

Figure 11:
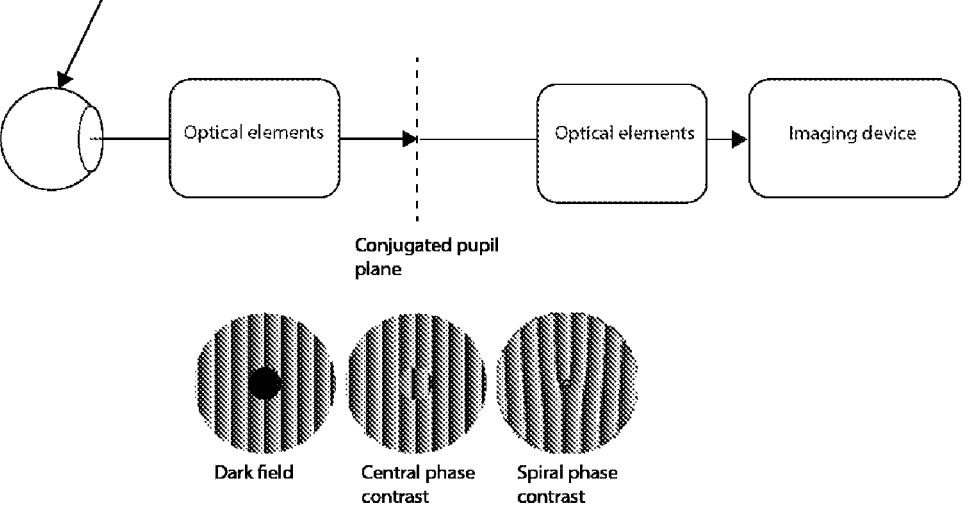
FIG. 11 shows an example of phase/absorption pattern in the Fourier/pupil plane to perform a filtering of the beam.

Referring to FIG. 11, this shows an example of phase/absorption pattern in the Fourier/pupil plane to perform a filtering of the beam. Three examples of pattern are given: dark field, central phase contrast and spiral phase contrast. The diffracted beam will filtered to obtain a high contrast image of the phase objects, such as the transparent cells of the retina.

A technological background of the present invention comprises the Prior Art discussed herein, and technical fields such as transscleral illumination, phase contrast imaging, dark field retinal imaging, and quantitative phase contrast microscopy, retinal tracking, large/small FOV.

The following lists a number of published works on devices for ophthalmology using transscleral illumination:

WO2017195163A1, System, method and apparatus for retinal absorption phase and dark field imaging with oblique illumination.

U.S. Pat. No. 7,387,385 B2, SURGICAL MICROSCOPE

US 2007/0159600 A1, TRANSCLERAL OPTHALMIC ILLUMINATION METHOD AND SYSTEM

US 20070030448 A1, ILLUMINATION UNIT FOR FUNDUS CAMERAS AND/OR OPHTHALMOSCOPES

A. Schalenbourg, L. Zografos "Pitfalls in colour photography of choroidal tumours." Eye. 2013; 27(2):224-229

Devrim Toslak, Damber Thapa, Yanjun Chen, Muhammet Kazim Erol, R. V. Paul Chan, and Xincheng Yao, "Trans-palpebral illumination: an approach for wide-angle fundus photography without the need for pupil dilation," Opt. Lett. 41, 2688-2691 (2016).

Previous works on dark field imaging for ophthalmology:

D. Scoles, Y. N. Sulai and A. Dubra "In vivo dark-field imaging of the retinal pigmentepithelium cell mosaic," Biomed. Opt. Exp. 4, 9, 1710-1723(2013)

T. Y. P. Chui, D. A. VanNasdale, and S. A. Burns, "The use of forward scatter to improve retinal vascular imaging with an adaptive opticsscanning laser ophthalmoscope," Biomed. Opt. Exp. 3, 10, 2537-2549(2012)

T. Y. P. Chui, T. J. Gast, and S. A. Burns, "Imaging of Vascular Wall Fine Structure in the Human Retina Using Adaptive Optics Scanning Laser Ophthalmoscopy," Invest Ophthalmol Vis Sci. 54, 7115-7124 (2013).

Previous works on retinal tracking:

U.S. Pat. No. 6,726,325 B2, TRACKING ASSISTED OPTICAL COHERENCE TOMOGRAPHY,

U.S. Pat. No. 6,736,508 B2, TRACKING ASSISTED OPTICAL PROCEDURE,

U.S. Pat. No. 8,857,988 B2 DATA ACQUISITION METHODS FOR REDUCED MOTION ARTIFACTS AND APPLICATIONS IN OCT ANGOGRAPHY

US 2014/0334707 A1, METHOD AND APPARATUS FOR IMAGE-BASED EYE TRACKING FOR RETINAL DIAGNOSTIC OR SURGERY DEVICE

U.S. Pat. No. 9,033,510 B2, SYSTEMIS AND METHODS FOR EFFICIENTLY OBTAINING MEASUREMENTS OF THE HUMAN EYE USING TRACKING.

Adaptive optics optical coherence tomography with dynamic retinal tracking', Biomed. Opt. Exp., 5(7), 2014.

U.S. Pat. No. 7,758,189 B2, STABILIZED RETINAL IMAGING WITH ADAPTIVE OPTIC S

'Adaptive optics scanning laser ophthalmoscope with integrated wide-field retinal imaging and tracking', J. Opt. Soc. Am. A, 27(11), 2010.

'Active eye-tracking for an adaptive optics scanning laser ophthalmoscope', Biomed. Opt. Exp., 6(7), 2015.

US 2004/0196399 A1, DEVICE INCORPORATING RETINA TRACKING.

Previous works on multi-scale retina imaging:

U.S. Pat. No. 8,696,122 B2 MULTI-FUNCTIONAL ADAPTIVE OPTICS RETNAL IMAGING.

WO2018197288A1 Système et méthode d'imagerie rétinienne multi-échelle.

Previous works on fourier filtering for phase imaging:

What spatial light modulators can do for microscopy, Lasers and Photonics Reviews 5, 81-101 (2011).

Spiral phase microscopy, Advances in Imaging and Electron Physics 146, 1-20 (2007); Ed. P. Hawkes, Academic Press (ISBN-13: 978-0-12-373908-7).

SLM-based off-axis Fourier filtering in microscopy with white light illumination, Opt. Exp., 20(14), 2012.

APPLICATIONS

Applications of the system include quantitative phase imaging of the retinal layer on top of the photoreceptors, between the inner and external limiting membranes, namely:

ILM—inner limiting membrane

RNFL—retinal nerve fiber layer

GCL—ganglion cell layer

IPL—inner plexiform layer

INL—inner nuclear layer

OPL—outer plexiform layer

ONL—outer nuclear layer

ELM—external limiting membrane

Next, the proposed system can be used to provide dark field or absorption-contrast images of the choroid and RPE (retinal pigmented epithelium), allowing for imaging of the choroidal tumors with enhanced contrast and choroidal microvasculature.

The proposed system can image transparent cells thanks to phase contrast in any of the layers mentioned above.

The retinal tracking allows for longitudinal patients' follow-ups of years, hence it enable a clinical application of the device.

The invention claimed is:

1. An ophthalmic illumination and imaging system with transscleral/transpalpebral illumination of the eye fundus, the system comprising:

a light-delivering device with a plurality of emitting areas; each of the emitting areas being configured to be independently controllable and directed towards the sclera of the intended eye to measure, providing transscleral oblique illumination of the eye fundus;

an active eye aberration correcting system; and wherein the system further comprises an imaging system configured to create multiple images of the eye fundus on multiple imaging sensors, said multiple sensor comprising a first retinal camera imaging the retina of the intended eye to measure with high resolution and a second retinal camera imaging said retina over a field of at least about 30°, wherein the system further comprises:

an active tracking system configured to track a movement of the eye fundus and configured to spatially stabilize at least one of the multiple eye fundus, wherein a measure of the movement of the eye is made using at least one of the multiple eye fundus images, wherein the correction of the eye movement is made using a 2-axis tip/tilt platform supporting the full wavefront corrector with an external rotation stage, or wherein the correction of the eye movement is made using a 2-axis tip/tilt platform supporting a mirror which does not include the wavefront corrector.

2. The system according to claim 1, wherein the retinal camera is configured to image the retina with a digital sampling smaller than 2 μm/pixel.

3. The system according to 1, wherein the retinal camera is configured to image the retina with a digital sampling of 20 μm/pixel.

4. The system according to claim 1, wherein the imaging system is configured to create multiple images of the eye fundus simultaneously on multiple imaging sensors.

5. The system according to claim 1, wherein the tracking system comprises a tracking sensor measuring the movement of the eye fundus and a tracking corrector configured to correct the at least one of the multiple images spatially stabilized for the movement.

6. The system according to claim 1, wherein the system further comprises a sequential switch configured to sequentially turn on one of the plurality of emitter areas at a time and enable a corresponding sequence in time of the eye fundus images created by the imaging system.

7. The system according to claim 1, wherein the active the eye aberrations correcting system comprises a wavefront sensor and a wavefront corrector.

8. The system according to claim 1, wherein the multiple images are produced with the light-delivering device.

9. The system according to claim 1, wherein a correction of the movement of the eye is made by tilting a mirror located at an optically conjugated eye pupil plane.

10. The system according to claim 1, wherein the correction of the eye movement is made using the tilting ablility of the wavefront corrector used for the active correction of the eye aberrations.

11. The system according to claim 1, wherein multiple imaging paths making the multiple eye fundus images are separated thanks to a beam splitter or a dichroic mirror.

12. The system according to claim 1, wherein the light-delivering device contains a light diffuser.

13. The system according to claim 12, wherein the diffuser integrated in the light-delivering device is used to obtain a few millimeters wide spot on the sclera or skin surface.

14. The system according to claim 12, wherein the diffuser is moving to produce temporal averaging of the speckle noise.

15. The system according to claim 1, wherein a wavelength of the light delivering device is chosen in the transmission range of the sclera-choroid-skin approximately from 400 nm to 1200 nm.

16. The system according to claim 1, wherein the light delivering device comprises a plurality of elementary components such as light emitting diode, superluminescent diode, organic light emitting diode, optical fibers.

17. The system according to claim 15 wherein individual emitting areas have a different temporal spectrum of emission from one to another.

18. The system according to claim 15, wherein individual emitting areas have a different angular spectrum of emission from one to another.

19. The system according to claim 1, further comprising a camera configured to record interference from one or several exit beams from the pupil and an additional reference beam extracted from the light-delivering device before entering the eye.

20. The system according to claim 1, wherein a non-uniform phase or absorption object is placed in a conjugated pupil plane to increase the phase contrast.

* * * * *